United States Patent

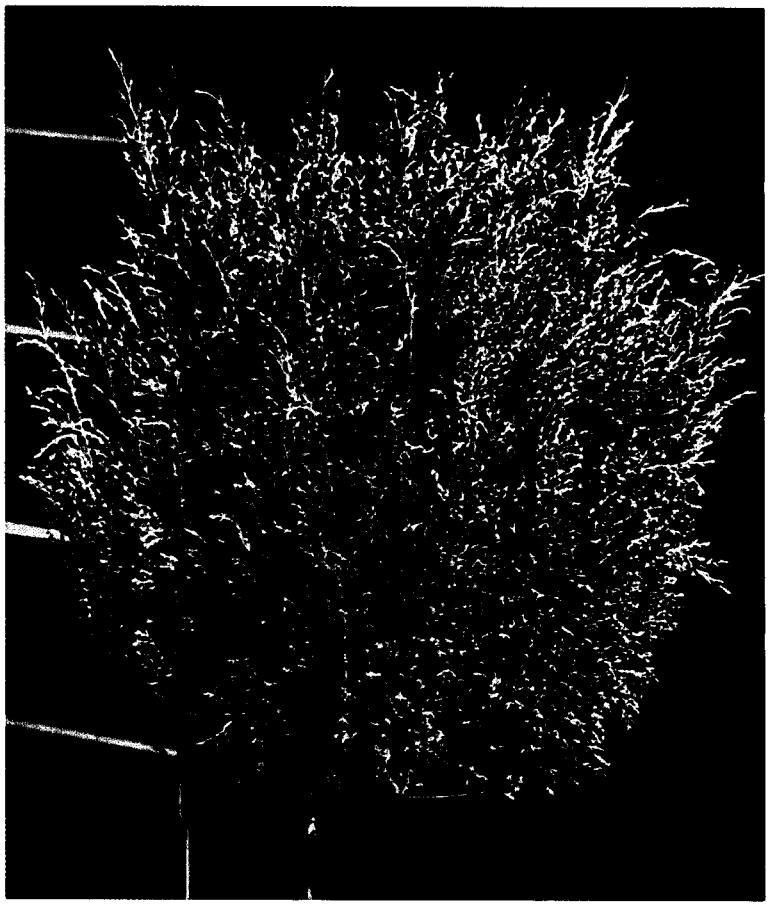

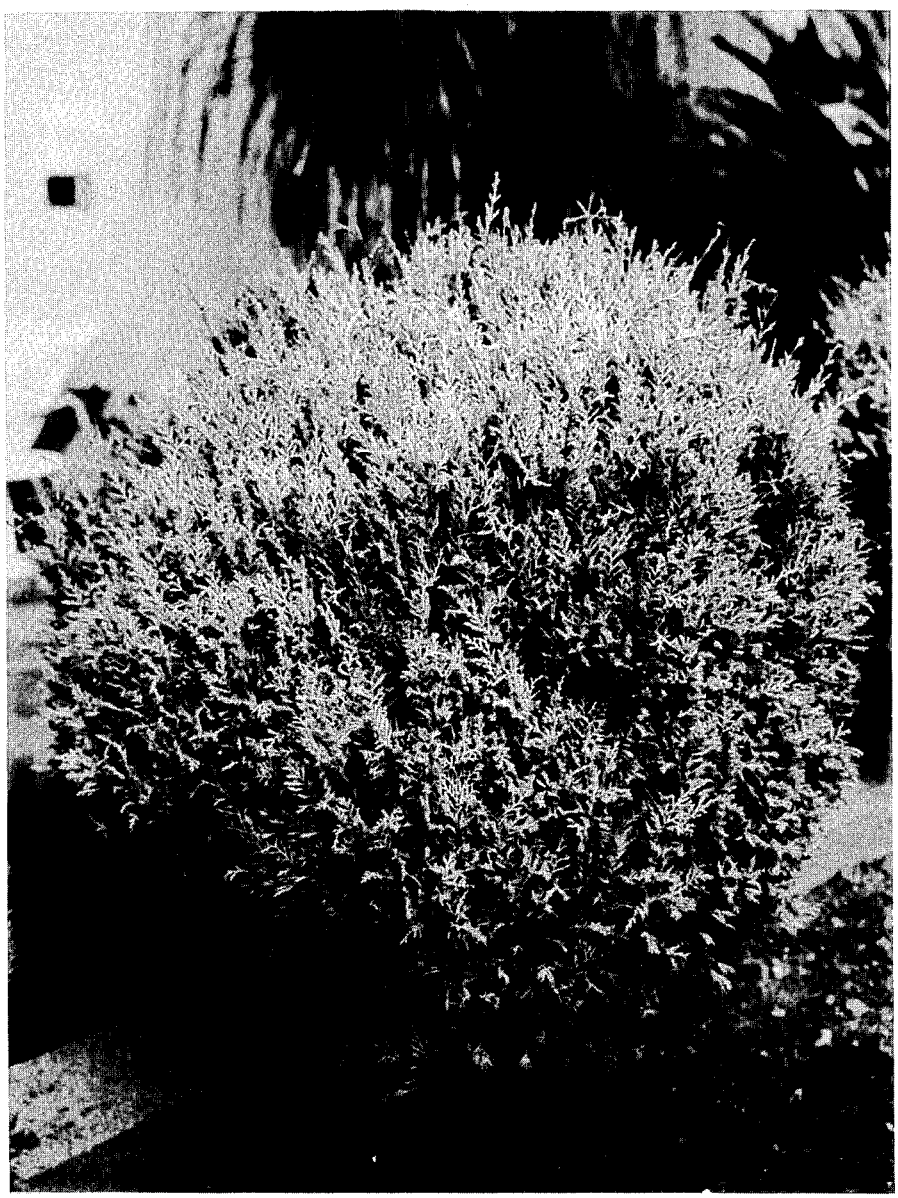

Plant Pat. 3,938
Patented Aug. 3, 1976

3,938
JUNIPER PLANT

Peter Mordigan, Sylmar, Calif., assignor to Select Nurseries, Inc., Brea, Calif.

Filed Apr. 7, 1975, Ser. No. 566,031
Int. Cl.[2] A01H *7/00*
U.S. Cl. Plt.—50 1 Claim

The present discovery relates to a new and distinct variety of the Cupressaceae family and more particularly to a plant of the Juniperus family.

The new variety was discovered by me as a sport on a plant in a group of *Juniperus armstrongi,* an unpatented variety, in 1963, growing on my property located at 15535 Bledsoe Street, Sylmar, Calif. Original cuttings from the plant sport were grafted to *Juniperus armstrongi* root stock. *Juniperus armstrongi* is a Chinensis type of Juniper.

The new variety is a very upright, compact shrub that reaches a height of about forty-eight inches and attains a width of about twenty-four inches. The time it takes for the plant to reach this mature condition after it has been asexually reproduced is usually about twelve years. *Juniperus armstrongi,* the plant on which the sport was discovered, is instead a semi-upright shrub that usually attains a height of four feet and has a spread of four feet.

The present variety has been asexually reproduced by me by means of cuttings. The resulting plants are slow growing and require considerable time to reach the dimensions set forth above for the new variety.

The new variety has been asexually reproduced during the years since its discovery and the asexual reproductions have exhibited the characteristics described above. This clearly shows that the new variety has become well established. The new variety has not been observed to produce any seed.

The accompanying drawings one in full color and one in black and white of a much older plant show the new variety of upright, very compact juniper. New leaves are generally narrow in width with the tips spinescent, however, the new leaves are frequently hidden by the mature foliage since they are developed on the lower portion of the branch close to the main stem or trunk.

The following is a detailed description of the new and distinct variety of juniper. To assist in the identification of the important colors of the new variety, the nomenclature adopted by the British Horticultural Colour Charts, these being "Horticultural Chart I" and "Horticultural Chart II," issued by Wilson Colour Ltd., in collaboration with the Royal Horticultural Society. Chart I set, shows "Copyright—Robert F. Wilson, 1938"; Chart II set, shows "Copyright—Robert F. Wilson, 1941."

THE PLANT

Locality where grown and observed: Sylmar, Calif.

General characteristics: The plant is an upright, very compact shrub.

Dimensions: The fully grown plant reaches a height of about forty-eight inches and a width of about twenty-four inches.

Branches: The plant has numerous upright branches that are of relatively fine caliper and are compactly arranged.

Trunk: The branches are attached to a central trunk of much larger caliper than the branches. The central trunk is brownish grey in color and is usually hidden by the compact branches and foliage.

Foliage: The plant has two types of foliage.

*Juvenile foliage.*—Size of leaves: The leaves are from one eighth inch to three sixteenths of an inch in length. The leaves are very narrow in width. Arrangement and form: The individual leaves are acicular, and generally opposite. The leaves are usually 2-ranked and are found at the lower end portion of the branch. The leaves are persistent. Color: Willow Green 000862/2.

*Mature leaves.*—Size of leaves: Adult leaves are much smaller than the juvenile leaves. Form and arrangement: The leaves are scalelike and are appressed. The groups of appressed leaves are more spread out on the stems than the juvenile leaves, and are also 2-ranked and generally opposite. Color: Mature leaves are Willow Green 000862/1.

*Texture.*—Both juvenile and adult leaves are stiff and spinescent and have a resinous texture.

*Tip behaviour.*—The tips of both the mature growth and the juvenile growth have a tendency to curl downwardly.

Cones: No cones have ever been observed.

Seed: No seed has been produced by the new variety.

I claim:

1. A new and distinct variety of juniper plant substantially as shown and described, characterized by its very compact upright growth, its thin needle-like juvenile leaves that are formed on the lower portion of each branch, the smaller adult leaves that are scale-like and appressed in groups, both juvenile and adult leaves being resinous in texture and having a tendency to curl downwardly at the tip portion, and by the absence of cones and seed.

No references cited.

ROBERT E. BAGWILL, Primary Examiner